United States Patent [19]

Stoub et al.

[11] Patent Number: 5,576,545

[45] Date of Patent: Nov. 19, 1996

[54] LINE SOURCE FOR ATTENUATION CORRECTION IN NUCLEAR MEDICINE STUDIES AND APPARATUS AND METHODS FOR USING THE SOURCE

[75] Inventors: Everett W. Stoub, Crystal Lake; William R. George, Chicago, both of Ill.

[73] Assignee: Siemens Medical Systems, Inc., Iselin, N.J.

[21] Appl. No.: 491,422

[22] Filed: Jun. 16, 1995

[51] Int. Cl.$^6$ .......................... G01T 1/161; G01T 1/166
[52] U.S. Cl. ........................................................ 250/363.04
[58] Field of Search ............................. 250/363.04, 369; 378/11, 9

[56] References Cited

U.S. PATENT DOCUMENTS 5,479,021  12/1995  Morgan et al. ..................... 250/363.04

OTHER PUBLICATIONS

Tan et al., "A Scanning Line Source For Simultaneous Emission and Transmission Measurements in Spect", Journal of Nuc. Med., vol. No. 34, 10, 1993, pp. 1752–1758.

Jaszczak et al., "Fast Transmission CT For Determining, Attenuation Mars Using a Collimated Line Source, Rotatable Air–Copper–Lead Attenuators and Fan–Beam Couimation", Journal of Nuc. Med. vol. 34 No. 9, 1993, pp. 1578–1586.

*Primary Examiner*—Carolyn E. Fields
*Assistant Examiner*—Edward J. Glick
*Attorney, Agent, or Firm*—Mark H. Jay

[57] ABSTRACT

In a system which corrects for attenuation artifacts in a SPECT study, a line source is parallel to the axis of rotation of the scintillation camera detector(s) and is scanned in a plane which is parallel to the detector. Advantageously, the line source is initially scanned at high speed across the detector to acquire preliminary transmission CT data and is subsequently scanned across the detector at lower speed to acquire additional transmission CT data. During rescanning, the shuttering of the line source, and/or the speed of the line source, is varied. This acquires transmission CT data which is more reliable and from which the attenuation of the patient may be more accurately calculated.

9 Claims, 12 Drawing Sheets

LINE SOURCE FOR ATTENUATION CORRECTION IN NUCLEAR MEDICINE STUDIES AND APPARATUS AND METHODS FOR USING THE SOURCE

BACKGROUND OF THE INVENTION

The invention relates to nuclear medicine, and more particularly relates to Single Photon Emission Computed Tomography ("SPECT") nuclear medicine studies. In its most immediate sense, the invention relates to attenuation correction of cardiac SPECT studies.

In a conventional SPECT (Single Photon Emission Computed Tomography) study of an organ such as the heart, a radioisotope (Tc-99m, Tl-201, for example) is administered to the patient and the radioisotope is taken up by the heart muscles. Then, the patient is placed in a scintillation camera system and one or more scintillation camera detectors are rotated about the long axis of the patient. These detectors pick up gamma radiation that leaves the patient, and the resulting data is used to form three-dimensional images ("SPECT images" or "tomographic images") of the distribution of the radioisotope within the patient.

Such three dimensional SPECT images can be calculated based on a set of two-dimensional images ("projections" or "projection images") acquired by the scintillation camera system; this calculation process is known as image reconstruction. The most commonly employed method of image reconstruction is known as "filtered backprojection". When filtered backprojection reconstruction is used to reconstruct SPECT images from scintigraphic projection images obtained from a scintillation camera, some well-known distortions introduce errors ("artifacts") in the result. One of the most important distortions is caused by attenuation of gamma radiation in tissue.

As a consequence of attenuation, image values in the various projections do not represent line integrals of the radioisotope distribution within the body. It is therefore necessary to correct for this, and the process for doing so in SPECT is known as attenuation correction.

Many techniques for attenuation correction in SPECT assume that the linear attenuation coefficient of the body is uniform and impose such uniformity as a mathematical constraint in the image reconstruction process. However, for a very important class of studies, namely cardiac SPECT studies, the linear attenuation coefficient of the body is in fact highly nonuniform. This is because lung tissue has a lower attenuation than do, e.g., the blood and other non-lung tissue.

Thus, in SPECT studies of, e.g., the heart, a SPECT reconstruction of the image of radioactivity within the heart will necessarily contain artifacts caused by the unequal attenuation coefficients of, e.g., the lungs and the body. Such artifacts also appear in SPECT cardiac images taken from obese patients and from large-breasted female patients.

It is known to measure the actual attenuation coefficients of body tissues by placing a line source of gamma radiation on one side of the body and measuring the transmission of the gamma radiation through the body as a function of direction, i.e. collecting transmission CT data, as the line source is scanned across the patient's body. However, existing line sources, and existing scintillation camera systems that use them, suffer from certain disadvantages.

One such disadvantage is that existing scanning line sources are mechanically awkward. Another such disadvantage is that it is very difficult to collect sufficient transmission CT data while at the same time not overburdening the camera. Still another such disadvantage is that it is difficult to calibrate the activity of the line source so as to produce a higher radiation density for use with obese patients or large breasted female patient and a lower radiation density for use with thin patients.

SUMMARY OF THE INVENTION

One aspect of the invention proceeds from the realization that in existing scintillation camera systems, the orientation of the line source causes unnecessary difficulties. In existing systems, the line source is normal to the axis of rotation of the camera system detector(s). This requires a relatively long line source that is difficult to mount on the camera gantry. In accordance with one aspect of the invention, the line source is reoriented by a 90° rotation so that it is parallel to the axis of rotation. This shortens the line source, and makes it easier to mount the line source to the camera gantry.

Another aspect of the invention proceeds from the realization that such a reoriented line source can, without undue mechanical complexity, be effectively shuttered so as to produce a varying density of radiation. This is impossible with prior art line sources. When a prior art line source is used, the ends of the line source will normally extend past the patient's body. (This is because the ends of the line source must be aligned with the edges of the detector, and the detector is usually large enough so that even large and obese patients can be imaged. As a result, there is usually a margin between the surface of the patient's body and the edge of the detector.) At the ends of the line source, radiation density delivered to the detector is at a maximum, while in the middle of the line source, radiation density delivered to the detector is at a minimum because the radiation is attenuated by the patient. With such a configuration, shuttering the line source at its ends would be mechanically difficult, because it would be necessary not only to adjust the degree of shuttering but also to adjust the positions along the line source at which the shuttering is brought about.

In accordance with another aspect of the invention, the reoriented line source can be shuttered to vary the radiation density that it produces. When, for example, the patient is not interposed between the source and the detector, the line source can be shuttered to produce a greatly reduced radiation density, thereby preventing the detector from being overwhelmed by an intense beam of radiation. When, later on during the scanning of the source, the patient is interposed between the source and the detector, the line source can be unshuttered to increase the number of counts detected by the detector and thereby increase the quantity of transmission CT data collected, thereby making possible a more precise determination of the attenuation caused by the patient's body.

In accordance with yet another aspect of the invention, the scanning speed of the source is variable. This permits the source to be scanned more slowly in regions of high attenuation (where more transmission CT data is necessary) and more quickly in regions of low attenuation (where less transmission CT data is necessary and indeed where transmission CT data must be reduced to avoid overwhelming the camera system).

In accordance with a method aspect of the invention, the scanning operation is carried out in two steps. In the initial step, the line source is quickly scanned across the patient in a shuttered state and preliminary transmission CT data is acquired. From this preliminary transmission CT data, regions of low attenuation are distinguishable from regions of high attenuation. Then, in the subsequent step, the scanning speed and/or the shuttered state of the line source is/are varied during a lower speed scan across the patient. Where more transmission CT data is necessary, the scanning speed is reduced and/or the line source is shuttered to a lesser degree; where less transmission CT data is necessary, the scanning speed is increased and/or the line source shuttered to a greater degree.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

As a preliminary matter, persons skilled in the art know that in a SPECT study, a collimated detector is rotated to a plurality of angularly separated stations around a patient. Typically, and for a conventional (180°) cardiac SPECT study, the detector will be rotated to 60 stations, each spaced 3° from the stations adjacent it. Likewise typically, the detector will dwell at each station for 25 seconds while acquiring emission data using the desired radioisotope (typically, Tc-99m or Tl-201).

If the SPECT study is to be attenuation corrected, transmission CT data must be acquired at each station. Conventionally, this is done by using a line source made of a different radioisotope (such as Gd-153) and acquiring, at each station, emission and transmission CT data simultaneously. This in turn is done by using two distinct energy windows, each corresponding to a one of the radioisotopes.

Figure 1:
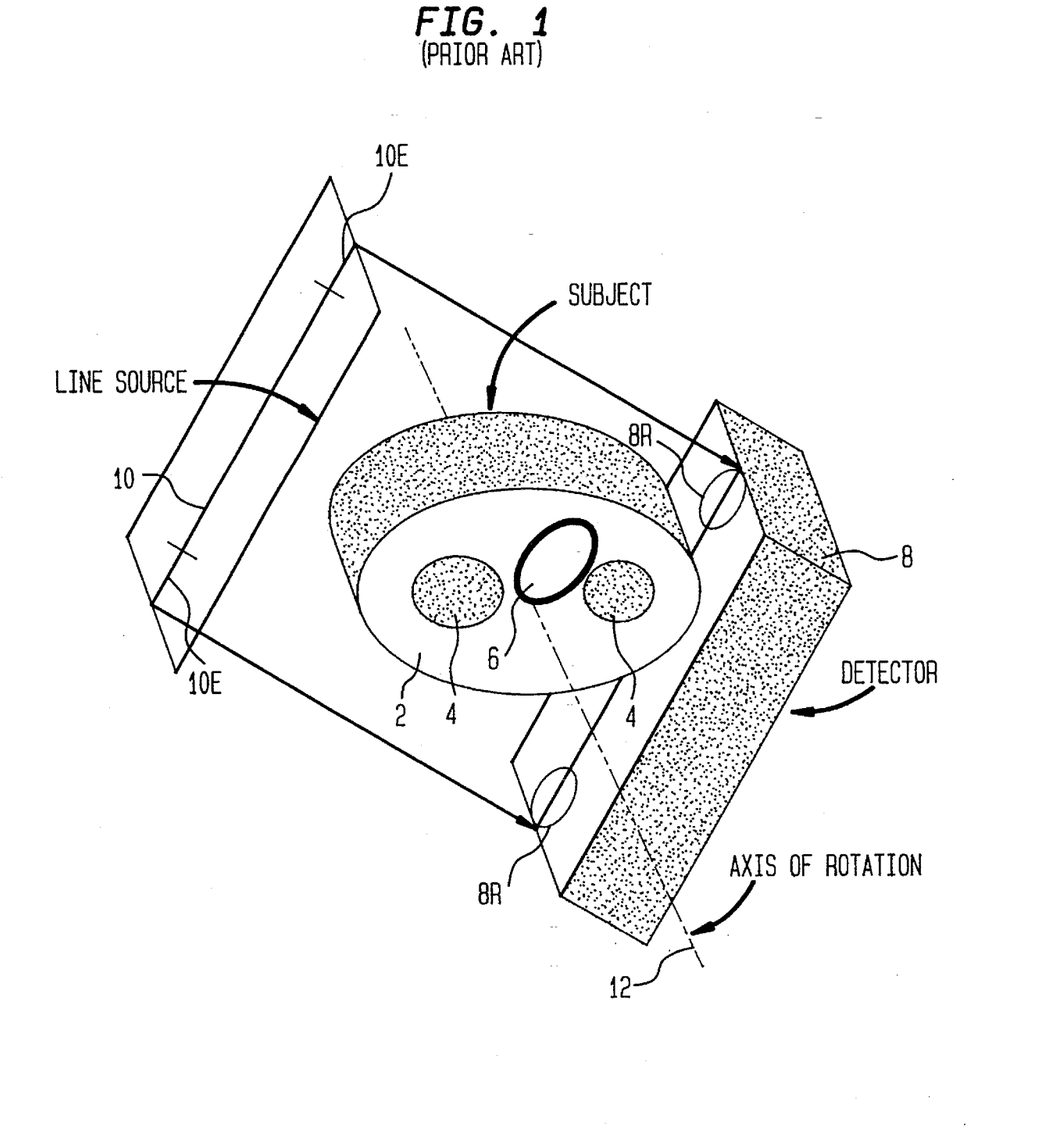
FIG. 1 schematically illustrates prior art scanning line sources as used in conventional scintillation camera systems.

In the following description, it will be assumed that transmission CT data is to be acquired in this manner using a line source of the scanning type, i.e. a line source that is moved parallel to the plane of the detector with which it is associated. FIG. 1 schematically shows a typical apparatus of this type.

A patient 2 has two lungs 4 and a heart 6. An attenuation-corrected SPECT cardiac study is to be carried out on the patient 2. To do this, the patient is interposed between the collimated detector 8 of the scintillation camera system (not otherwise shown) and a line source 10. The line source 10 is perpendicular to the axis 12 about which the detector 8 rotates, and is scanned parallel to the axis 12 to acquire transmission CT data from the patient 2. In this case, the scanning proceeds along the patient's length, i.e. from the patient's waist towards the patient's chin or vice versa. To make sure that transmission CT data is acquired for the entire surface of the detector 8, the line source 10 is required to be as long as the long dimension of the detector 8. Since in almost all cases the patient 2 to be studied will be narrower than this dimension, there will almost always be end regions 10E of the source 10, which are separated from the corresponding detector regions 8R of the detector 8 only by air gaps.

As a result, when conventional apparatus such as is illustrated in FIG. 1 is employed, "hot spots" are created at regions 8R. This is because radiation from the end regions 10E of the source 10 is not attenuated by the patient 2. The radiation density produced by the source 10 must consequently be limited; only by doing this is it possible to prevent the camera system from being overwhelmed by the hot spots at regions 8R of the detector 8.

Figure 2:
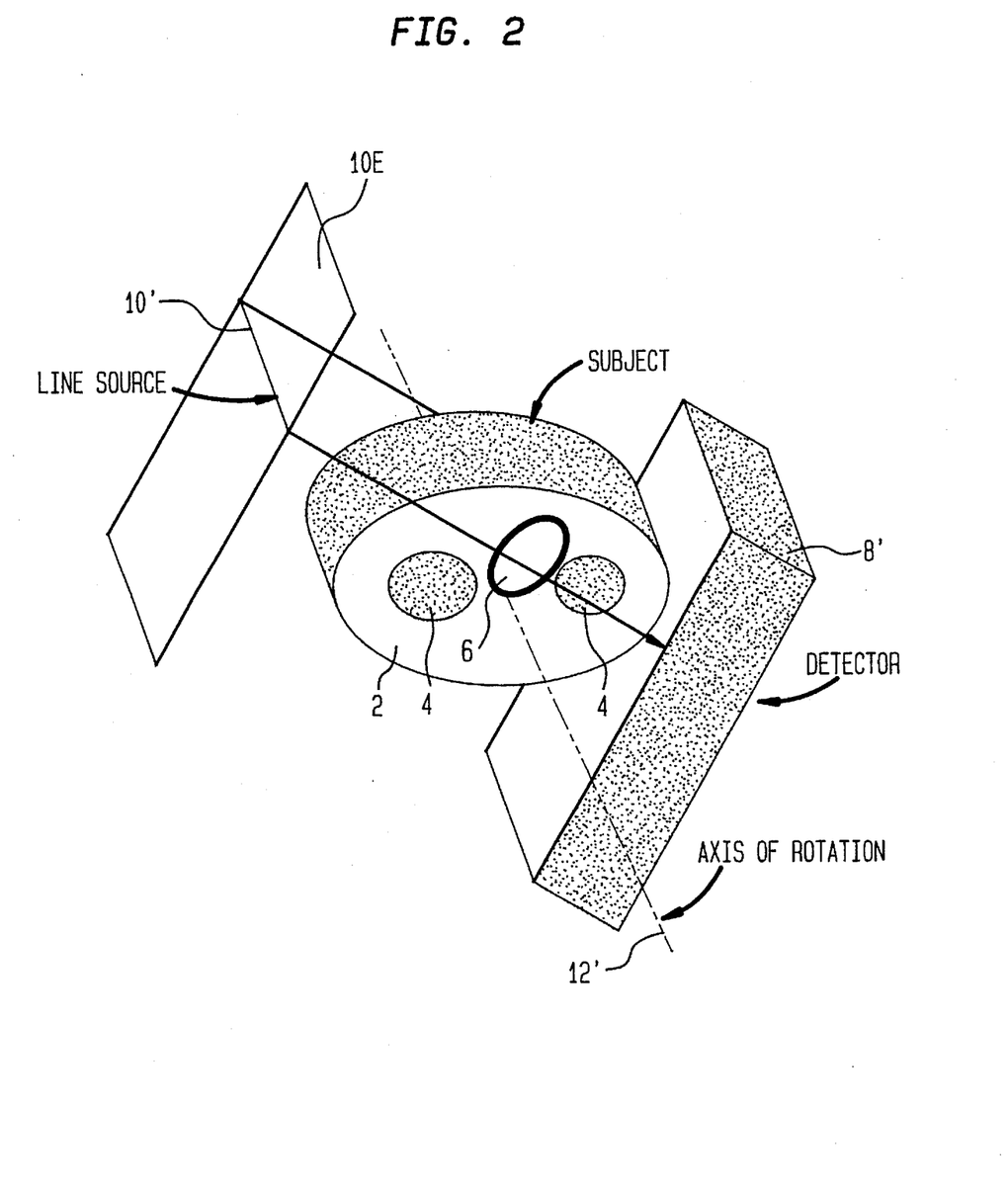
FIG. 2 schematically illustrates a scanning line source in accordance with the invention.

In accordance with one aspect of the invention, illustrated in FIG. 2, the line source 10' is parallel to the axis 12' of the camera system. This prevents the ends of the line source 10' from producing "hot spots" on the detector 8'. Furthermore, when the line source 10' is scanned across the patient 2, the scanning proceeds transversely across the patient 2, i.e. from the patient's left side to the right side, or vice versa.

Figure 3:
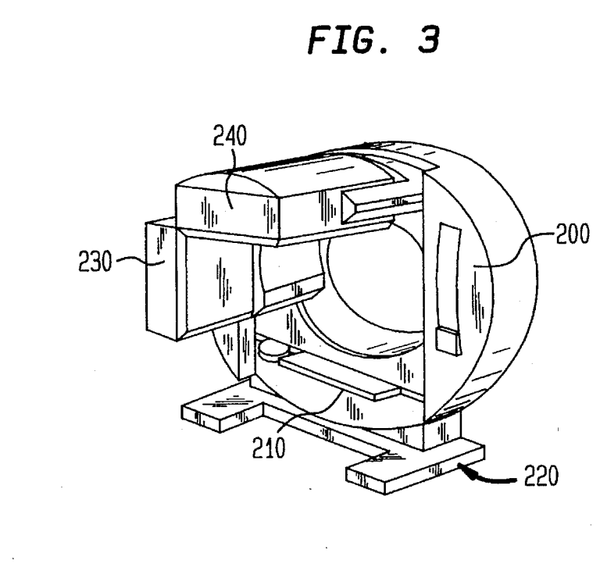
FIGS. 3 and 4 schematically illustrate two scanning line sources in accordance with the invention, installed on a scintillation camera gantry and shown respectively in the stowed and deployed positions.
Figure 4:
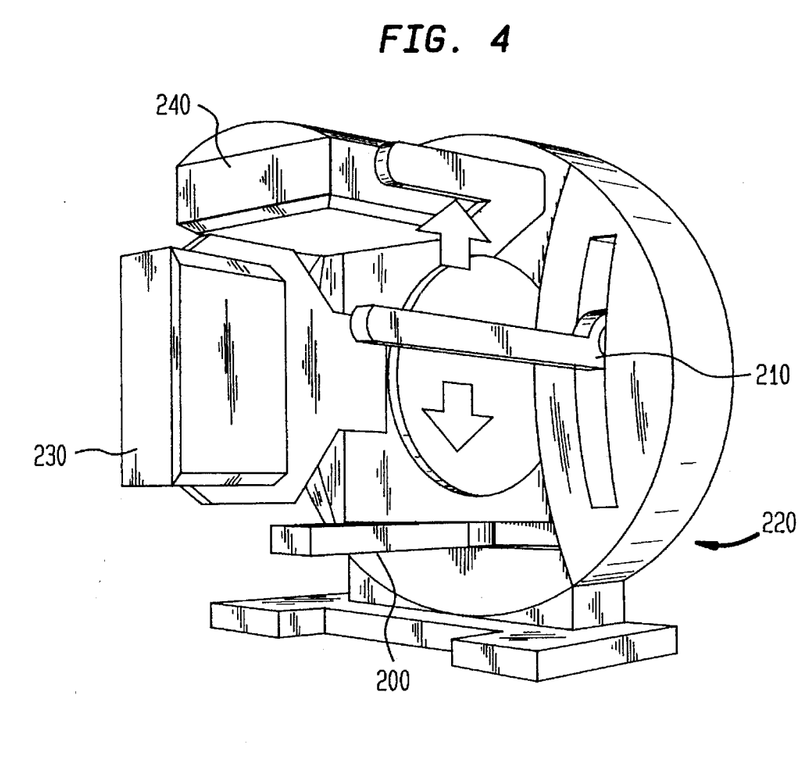

In FIGS. 3 and 4, line sources 200 and 210 are installed on a camera gantry generally indicated by reference numeral 220. The line sources 200 and 210 are opposed to rectangular detectors 230 and 240 respectively; the detectors 230 and 240 are identical and the line sources 200 and 210 are also identical. Each of the line sources 200, 210 is as long as the shorter dimension of the detector 230, 240 to which it corresponds. As shown, the gantry 220 is configured so the detectors 230 and 240 are at right angles to each other; this is the preferred configuration for cardiac studies. As shown in FIG. 3, the line sources 200 and 210 are stowed; in this position, they do not project outward from the gantry 220 and are not used for attenuation correction. However, as shown in FIG. 4, the line sources 200 and 210 are deployed; in this position, they do project outward from the gantry 220 and are scanned parallel to the longer dimension of the detectors 230 and 240.

Figure 5:
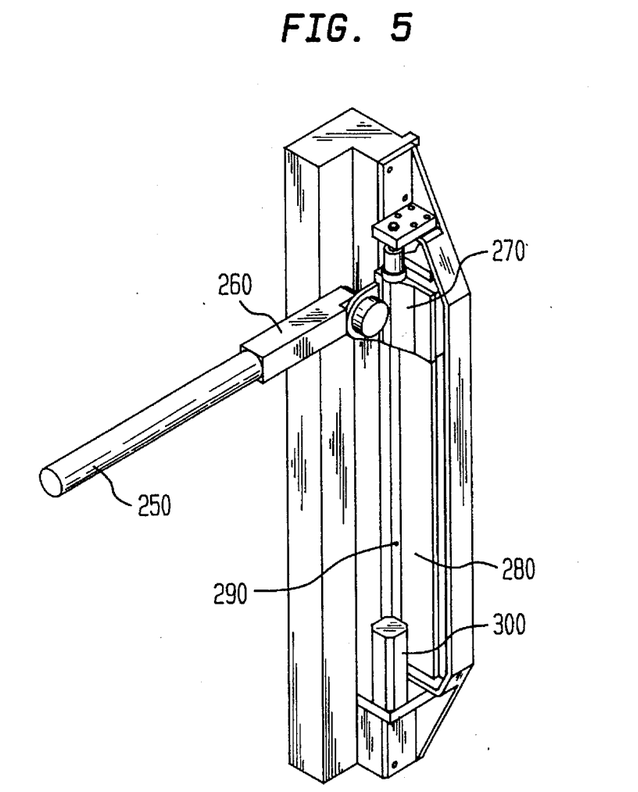
FIGS. 5 and 6 schematically illustrate a scanning line source in accordance with the preferred embodiment of the invention in the deployed and stowed positions.
Figure 6:
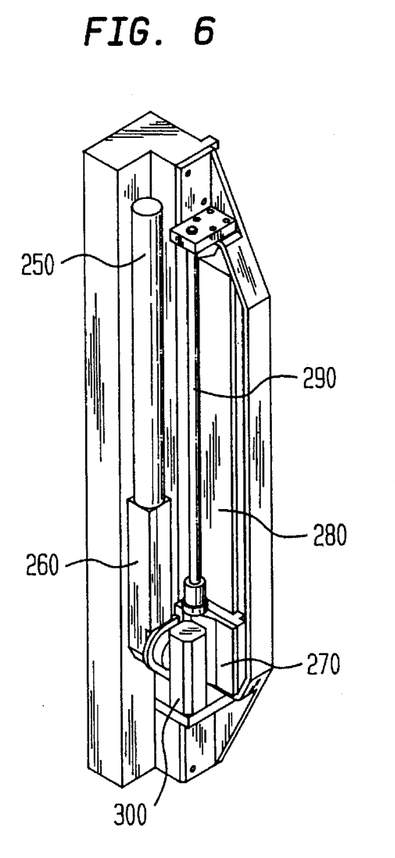

FIGS. 5 and 6 show the general construction of a line source 200 in accordance with the preferred embodiment of the invention. The line source 200 has a distal radiation-emitting portion 250; as will be described below in more detail, the density of the radiation emitted from the portion 250 can be changed using a shutter mechanism that is controlled by apparatus within a proximal portion 260. The portion 260 is pivotally secured to a carriage 270.

The carriage 270 engages with a track 280 and is constrained to move along the track 280. The track 280 is parallel to the longer dimension of the particular detector (not shown in these Figures, but in this instance detector 230) that corresponds to the line source 200. The carriage 270 also engages with a threaded rotatable shaft 290 that is parallel to the track 280 and that is rotated by a motor 300. Thus, the direction of movement of the carriage 270 (i.e. the scan direction of the line source 200) is determined by the direction of rotation of the motor 300, and the speed of the carriage 270 (i.e. the scan speed of the line source 200) is determined by the speed of the motor 300.

In the stowed position of the line source 200, the portion 250 is parallel to the track 280 and shaft 290. In this position, the portion 250 is generally parallel to, and located within, the exterior housing of the gantry 220. In the deployed position of the line source 200, the portion 250 is perpendicular to the track 280 and shaft 290; in this position the portion 250 projects outwardly and at right angles to the exterior housing of the gantry 220. When deployed, the distal end of the portion 250 is aligned with one of the longer sides of the detector 230 and the proximal end of the portion 250 is aligned with the opposite longer side of the detector 230. When the carriage 270 is at one end of the track 280 and the line source 200 is in the deployed position, the portion 250 is aligned with one of the shorter sides of the detector 230; when the line source 200 is in the deployed position and the carriage 270 is at the other end of the track 280, the portion 250 is aligned with the other shorter side of the detector 230. In this way, movement of the carriage 270 from one end of the track 280 to the other causes the line source 200 to scan completely across the detector 230.

In accordance with the preferred embodiment of the invention, the radiation density produced by the line source 200 is variable, and the speed with which the line source 200 scans across the patient, may be varied as well. The mechanism by which the radiation density is varied will be discussed next with reference to FIGS. 7 and 8; thereafter, the manner in which the radiation density and the scan speed are co-varied will be explained.

Figure 7:
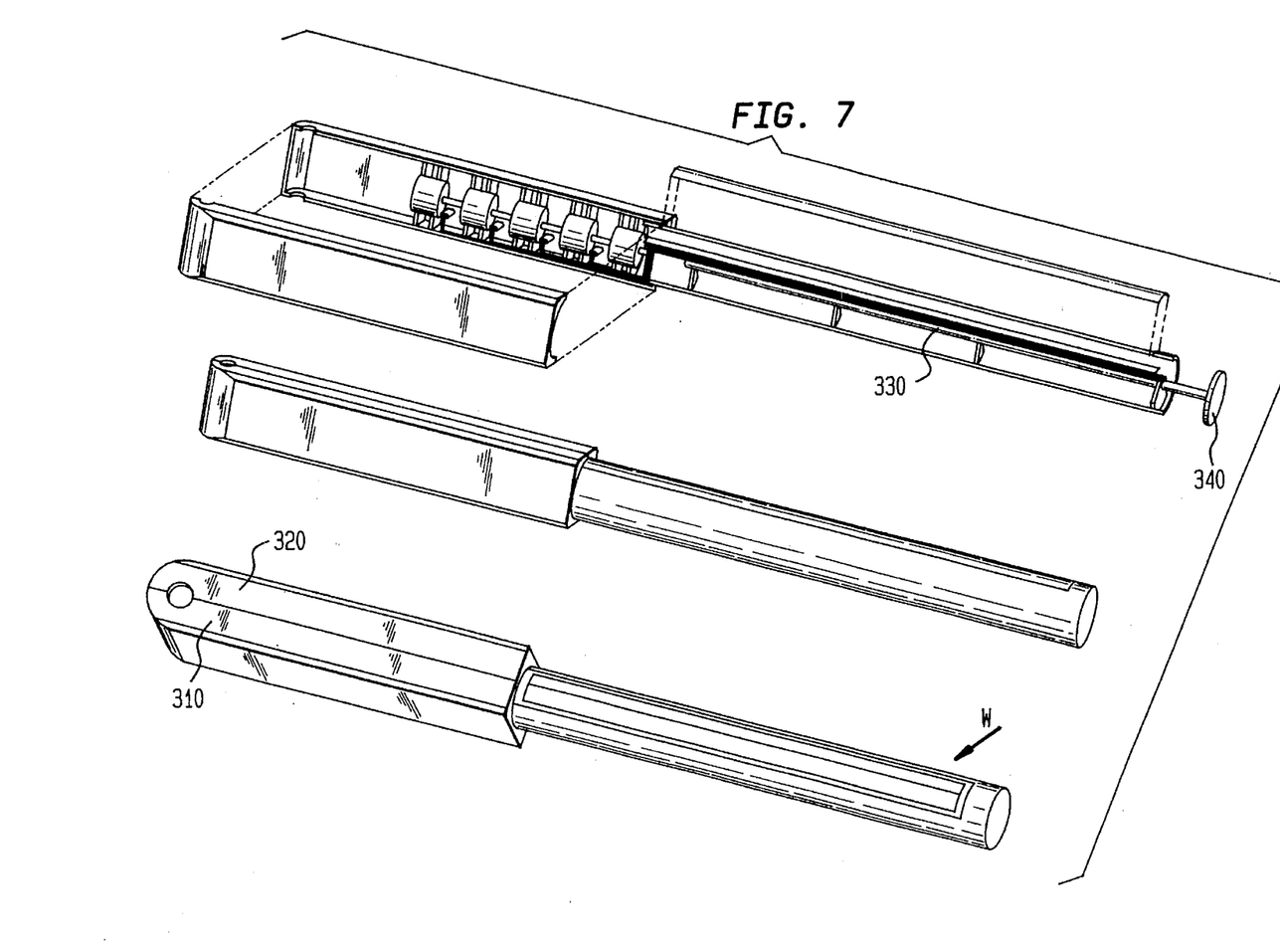
FIGS. 7, 8 and 9 schematically illustrate the interior construction of a scanning line source in accordance with the preferred embodiment of the invention.
Figure 8:
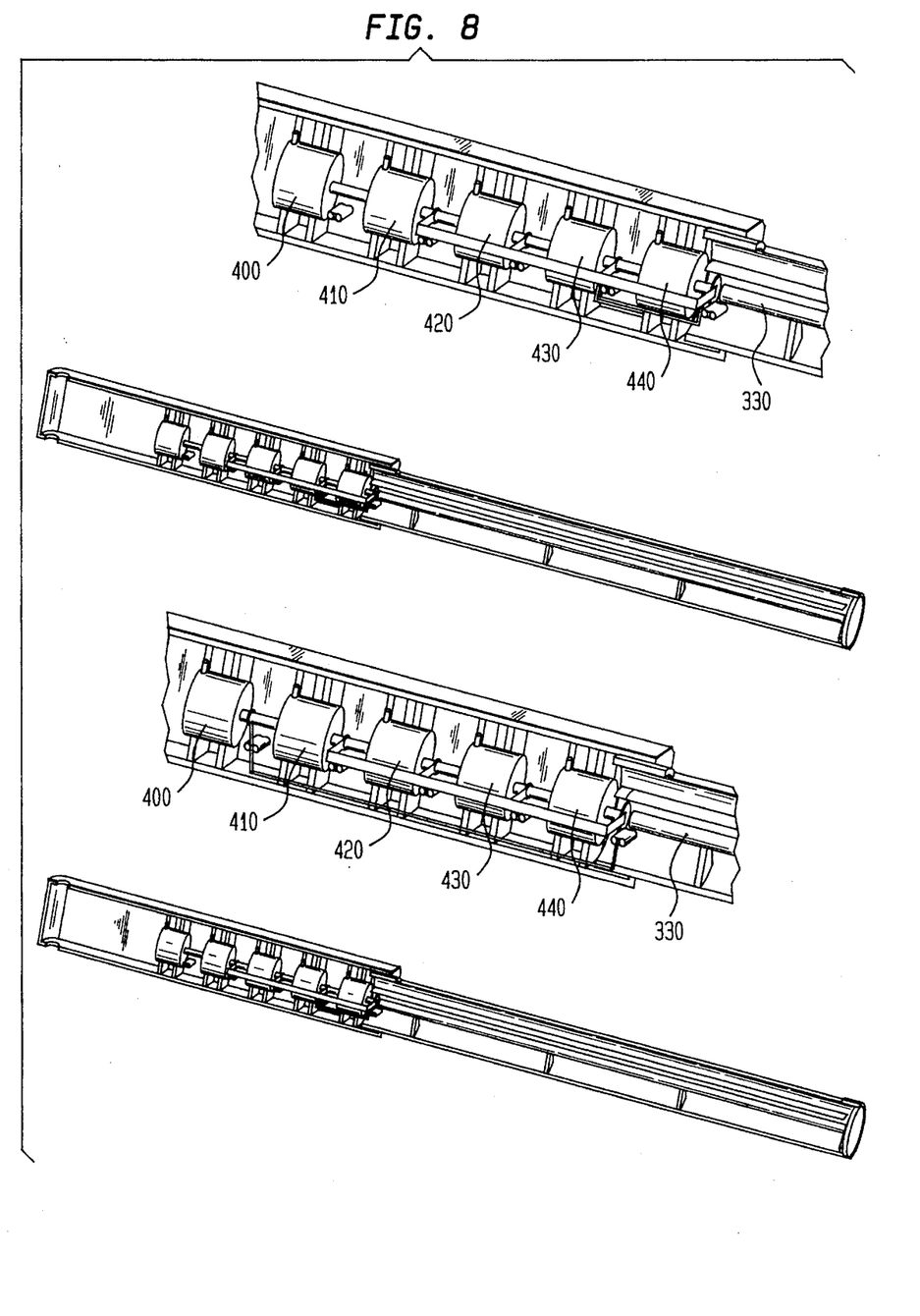
Figure 9:
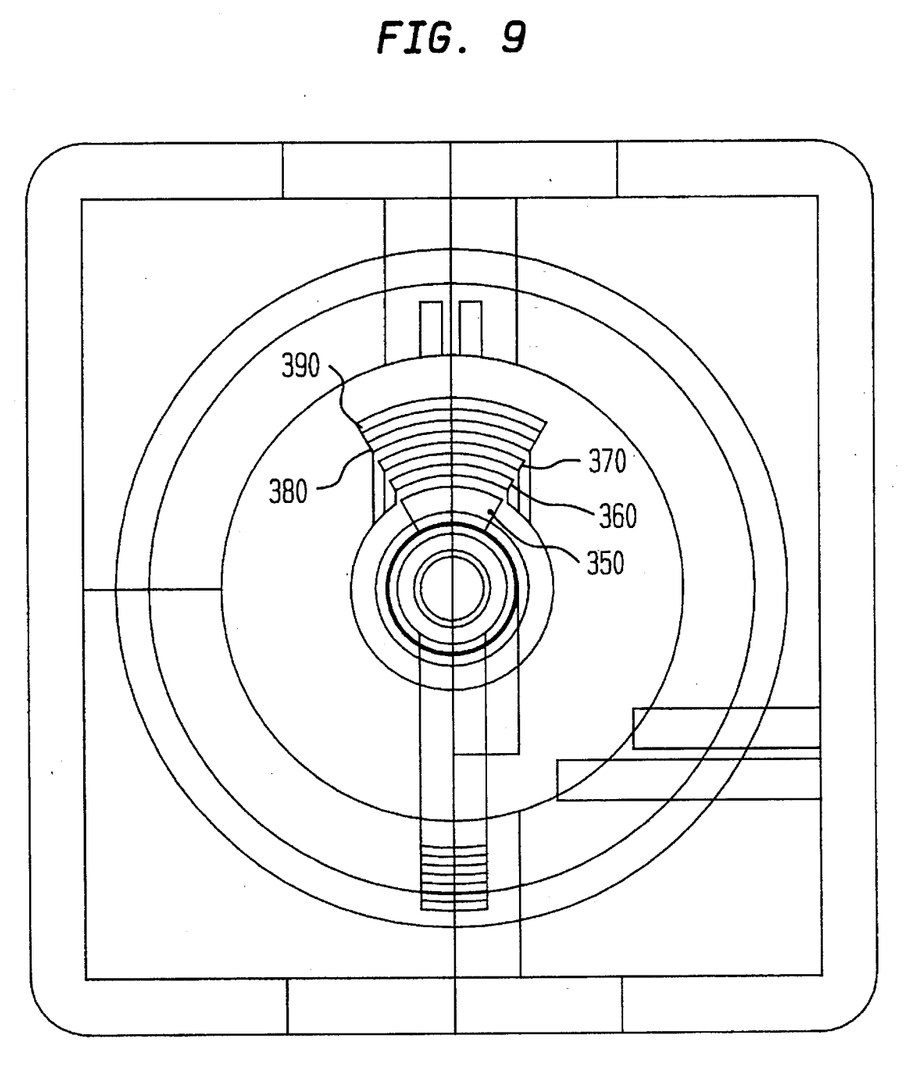

The portions 250 and 260 are formed from two housing halves 310 and 320. The housing halves 310 and 320 are made of a material that is opaque to gamma radiation, and are axially notched adjacent the distal end of the portion 250; this produces a rectangular window region W through which all radiation is constrained to exit the line source 200. The radiation is emitted from radioactive material contained in an elongated, tubular container 330 that extends along the central axis of the portions 250 and 260. The container 330 is attached at one end to a disc 340, which forms the distal end of the portion 250 and serves as a handle. When the radioactive material in the container 330 has decayed to the point where the container 330 must be replaced, the disc 340 is grasped, the container 330 is withdrawn and a replacement container 330 is introduced into the line source by holding the disc 340 on the replacement unit.

To vary the radiation density through the window W, one or more shutters are interposed between the window W and the container 330. In the preferred embodiment, there are five such shutters 350, 360, 370, 380 and 390. Each of the shutters 350, 360, 370, 380 and 390 is shaped as a portion of a cylinder and all the shutters 350 . . . 390 are concentric and pivotally supported so as to pivot about 90° about the axially directed container 330.

Each of the shutters 350 . . . 390 is spring-biased to an unactuated position and is moved to an actuated position by a corresponding one of the rotary solenoids 400 . . . 440. When a solenoid (e.g. solenoid 400) is unenergized, the corresponding shutter (shutter 350, in this instance) is spring-biased to an unactuated position in which it covers the window W. When a solenoid (e.g. solenoid 400) is energized, the corresponding shutter (shutter 350, in this instance) is moved to an actuated position where it does not cover any part of the window W. It may therefore be understood that the radiation density through the window W can be adjusted by actuating one or more of the shutters 350 . . . 390 (i.e. by energizing one or more of the solenoids 400 . . . 440).

In accordance with the preferred embodiment, the radially innermost shutter 350 is made of a material that completely prevents radiation from the container 330 from exiting the window W. This is a safety feature that prevents radiation from being emitted from the line source 220 in the event of a power failure or a malfunction. Also in accordance with the preferred embodiment, the next outermost shutter 360 has an attenuation of X, the next outermost shutter 370 has an attenuation of 2X and the next outermost shutters 380 and 390 have attenuations of 4X and 8X respectively. This scheme permits the radiation density from the line source 200 to be attenuated in steps of X between 0 and 15X by suitably energizing one or more of the solenoids 410 . . . 440.

Before describing a method in accordance with the preferred embodiment of the invention, the problem which this method addresses will be described first in connection with FIGS. 10A, 10B and 10C.

Let it be assumed that a line source (such as the line source 200) is swept across a detector at constant speed. Let it also be assumed that the radiation density produced by the line source is (by appropriate shuttering) held constant at a value that does not overwhelm the camera system with counts. Let it finally be assumed that a cardiac SPECT study is to be carried out, that during the study the detector dwells for 25 seconds at each radial station and that the line source moves at a speed which is calculated to sweep across the detector in exactly 25 seconds.

It will be readily apparent that the count density (number of valid scintillation events per unit area of the detector) recorded by the camera system for a particular detector region provides a rough measure of quality of the transmission CT data acquired in that region during scanning of the line source. The higher the recorded count density, the more accurately can the attenuation coefficient of the patient be determined, and the more artifact-free can the final SPECT image be made. As will be seen below, a conventional method for acquiring transmission CT data produces transmission CT data of unacceptably poor quality.

Figure 10A:
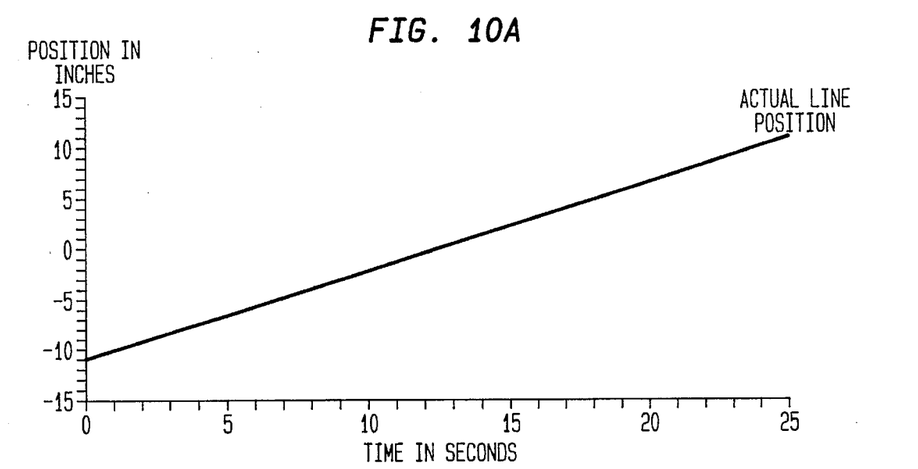
FIGS. 10A, 10B and 10C are graphs indicating data acquisition in attenuation correction systems in accordance with the prior art.
Figure 10B:
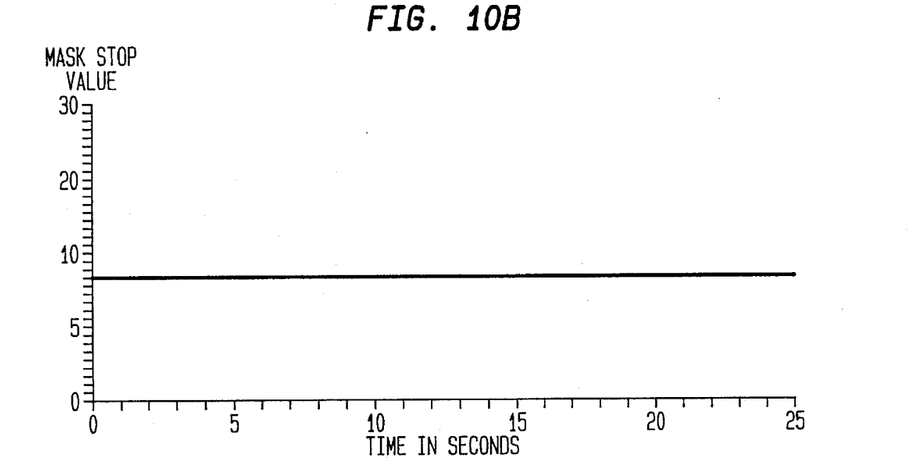
Figure 10C:
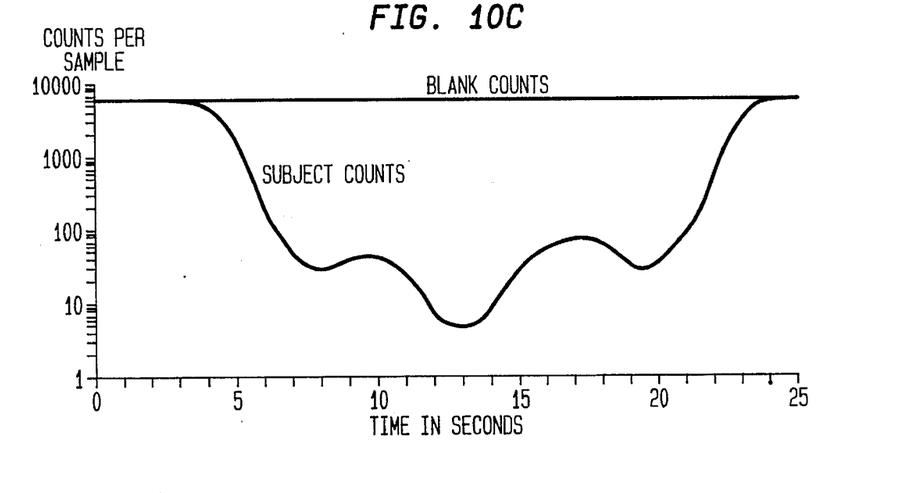

As can be seen by a comparison between FIGS. 10A, 10B and 10C, during the initial portion of a conventional attenuation correction scan the registered count rate (number of valid events per unit time) at the detector is at a maximum. This is because the line source starts out at a position where the patient does not attenuate the radiation produced by the line source before that radiation is incident upon the detector. Then once the line source moves to a position where its radiation passes through the patient before becoming incident on the detector, the registered count rate begins to decrease.

This decrease in count rate then ceases when the line source moves to a position where its radiation passes through the patient's lungs (which, as discussed above, are more transparent to gamma radiation than fatty tissue). While the line source is directing radiation through the lungs, the count rate climbs to a local maximum; the count rate subsequently drops as the radiation beam passes by the patient's lungs and through the patient's fatty tissue. Thereafter, the count rate climbs to its initial maximum value once the line source has moved to its final extreme position (in which the patient is not interposed between the exit window of the line source and the detector).

By using a set of reasonable assumptions (e.g. the radioisotope used in the line source, the shuttering of the source itself, the size of the detector, the speed with which the line source is scanned across the detector, the attenuation coefficients of the patient's lungs and fatty tissue etc.) in a computer model which takes the above-described phenomena into account, the minimum count density at the detector (and therefore the quality of the transmission CT data acquired) can be estimated. For a conventional attenuation correction system, the minimum count density at the detector is less than 1 count per square centimeter. Such a count density is not sufficiently more intense than background radiation as to provide a statistically reliable basis for calculating the attenuation coefficients applicable to the patient. For this reason, such a count density provides transmission CT data of insufficiently high quality; such data cannot be relied upon to produce SPECT images which are free of attenuation artifacts.

Figure 11:
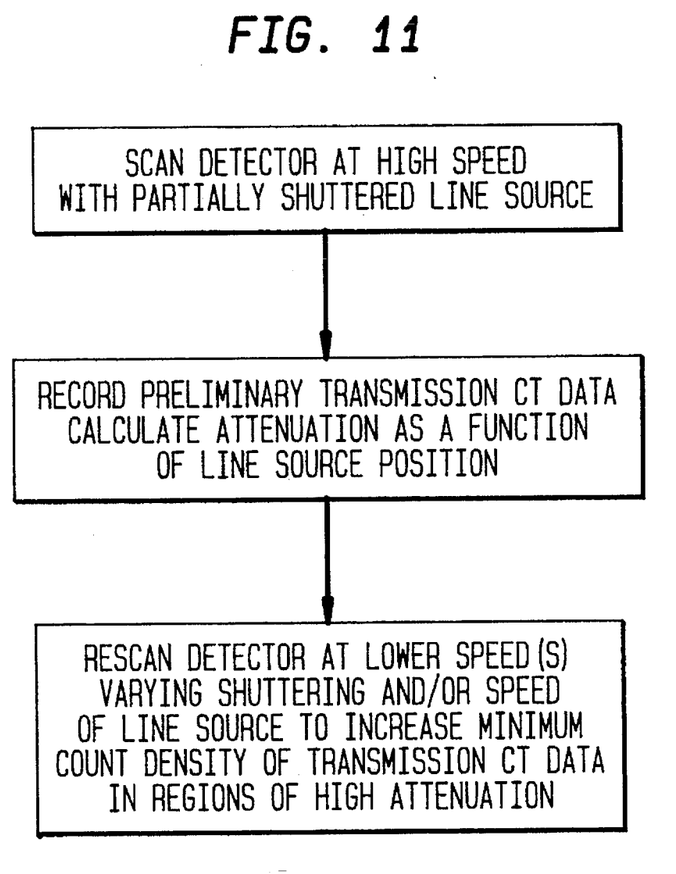
FIG. 11 is a flow chart of a preferred method in accordance with the invention.

In accordance with the preferred embodiment of the method of the invention as illustrated in the FIG. 11 flowchart, collection of transmission CT data takes place in two steps. During each step, the line source is scanned completely across the detector. During the first step, the line source is scanned quickly while in a partially shuttered state. The counts registered at the detector during this first step are used to distinguish regions of higher attenuation from regions of lower attenuation.

During the second step, the line source is rescanned, but at such minimum speed(s) as will cause the entire detector to be scanned during the time remaining. For example, if a cardiac SPECT study is set up so that each detector dwells at a particular station for twenty five seconds, and if the first step occurs in five seconds, the line source will then be driven at such speed(s) during the second step that the rescan of the entire detector will be completed in twenty seconds.

During the second step, the radiation density produced by the line source is varied by changing the shuttering of the line source. In regions where attenuation is high, the line source is opened up so that count density in such regions is increased. In regions where attenuation is low, the line source is closed down so that count density in such regions does not saturate the camera system. This permits more events to be registered by the detector in regions where such additional events are necessary to obtain statistically reliable transmission CT data.

In accordance with one preferred embodiment of a method in accordance with the invention, the speed of the line source during the second step is held constant as the shuttering of the line source is varied. However, this is not necessary, and in a second preferred embodiment of the invention the speed of the line source during the second step is varied as well.

Figure 12A:
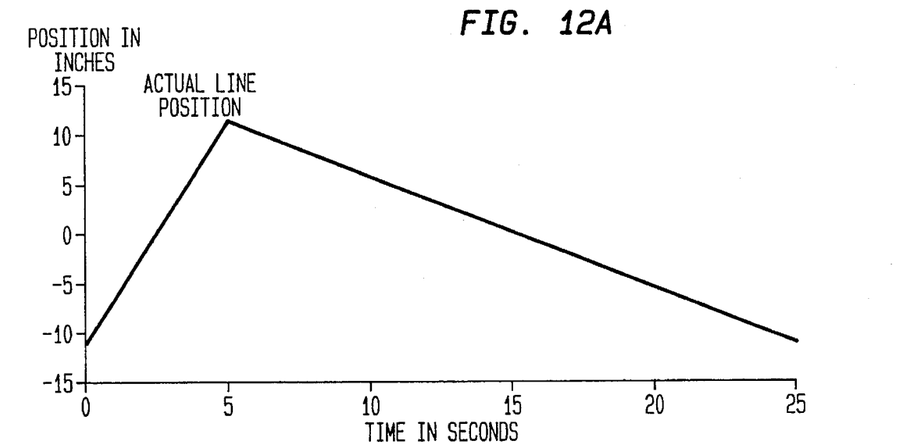
FIGS. 12A, 12B and 12C are graphs indicating data acquisition accordance with a first preferred method embodiment of the invention.
Figure 12B:
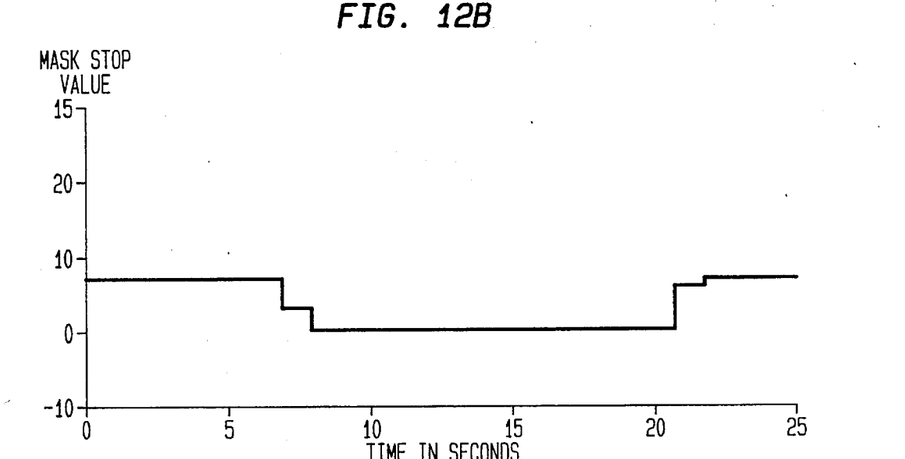
Figure 12C:
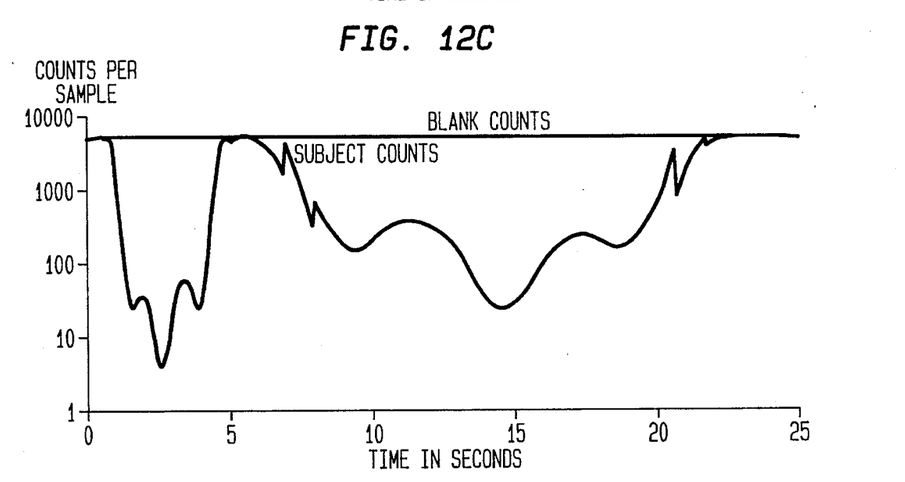

Turning now to the first preferred method embodiment as illustrated in FIGS. 12A, 12B and 12C, the above described first step is carried out over a five second interval with the line source partially shuttered at an attenuation factor of 8X. (The five second duration of this step is not part of the invention; this step may last for a shorter or a longer time.) During this step, the counts registered at the detector are processed to determine the attenuation coefficient of the patient as a function of the location of the line source.

The second step is then carried out over the remaining twenty seconds, at a lower and constant speed and in the reverse direction across the detector. As radiation from the line source is attenuated by the patient's fatty tissue, the source is progressively opened up in steps until it is completely unshuttered. The source then remains completely unshuttered for more than 50% of the second step, until the count density at the detector begins to rise as the line source approaches the surface of the patient's body. At this point, the source is partially shuttered once again.

In the embodiment shown in FIGS. 12A, 12B and 12C, the minimum count density exceeds 4.7 counts per square centimeter. This data is statistically meaningful, and can be expected to produce statistically meaningful information relating to the attenuation of the patient.

Figure 13A:
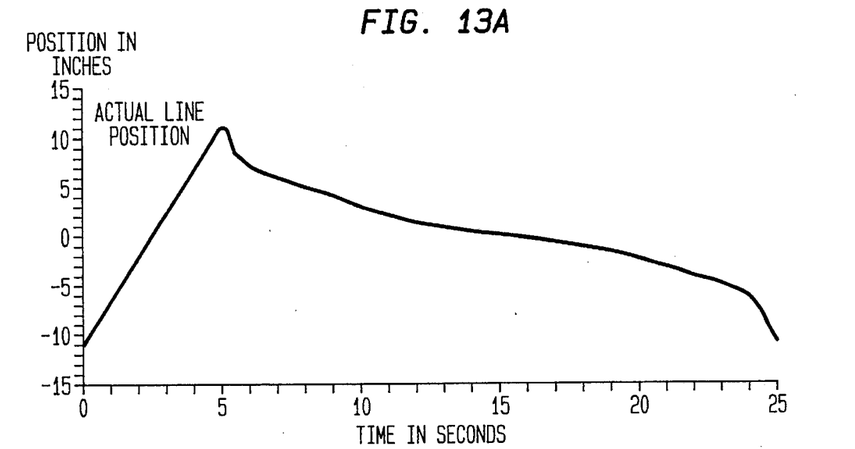
FIG. 13A, 13B and 13C are graphs indicating data acquisition in accordance with a second preferred method embodiment of the invention.
Figure 13B:
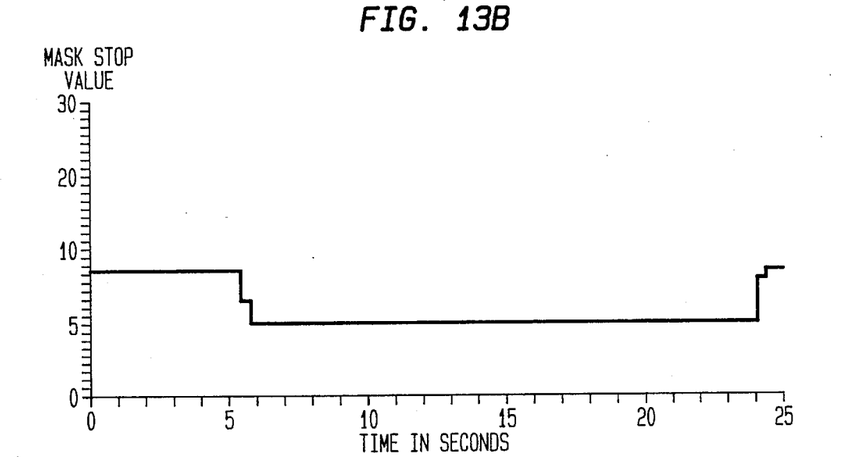
Figure 13C:
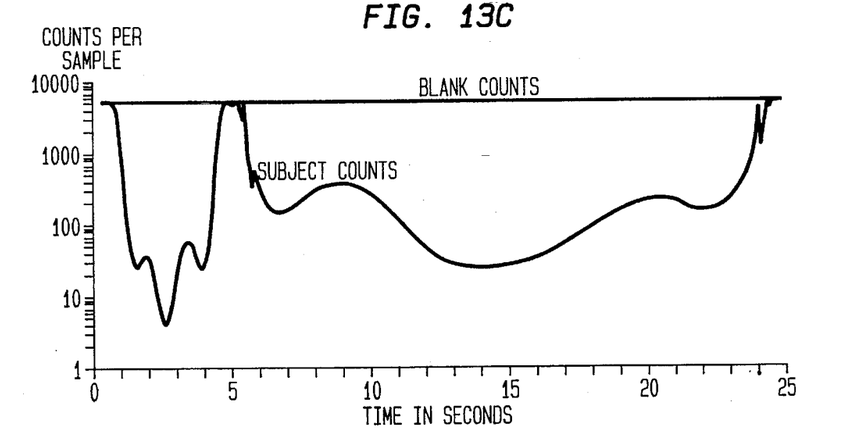

In a second preferred embodiment of a method in accordance with the invention, both the shuttering of the line source and the speed of the line source are varied during the rescan which is carried out during the second step. As can be seen in FIGS. 13A, 13B and 13C, the line source moves more quickly at the ends of the rescan (when radiation emitted by the line source is not attenuated by the patient). This leaves more time available for rescanning the center domain of the detector, permitting the line source to be moved more slowly in that region. The result is to further increase the minimum count density, this time to over 9.7 counts per square centimeter.

Figure 14:
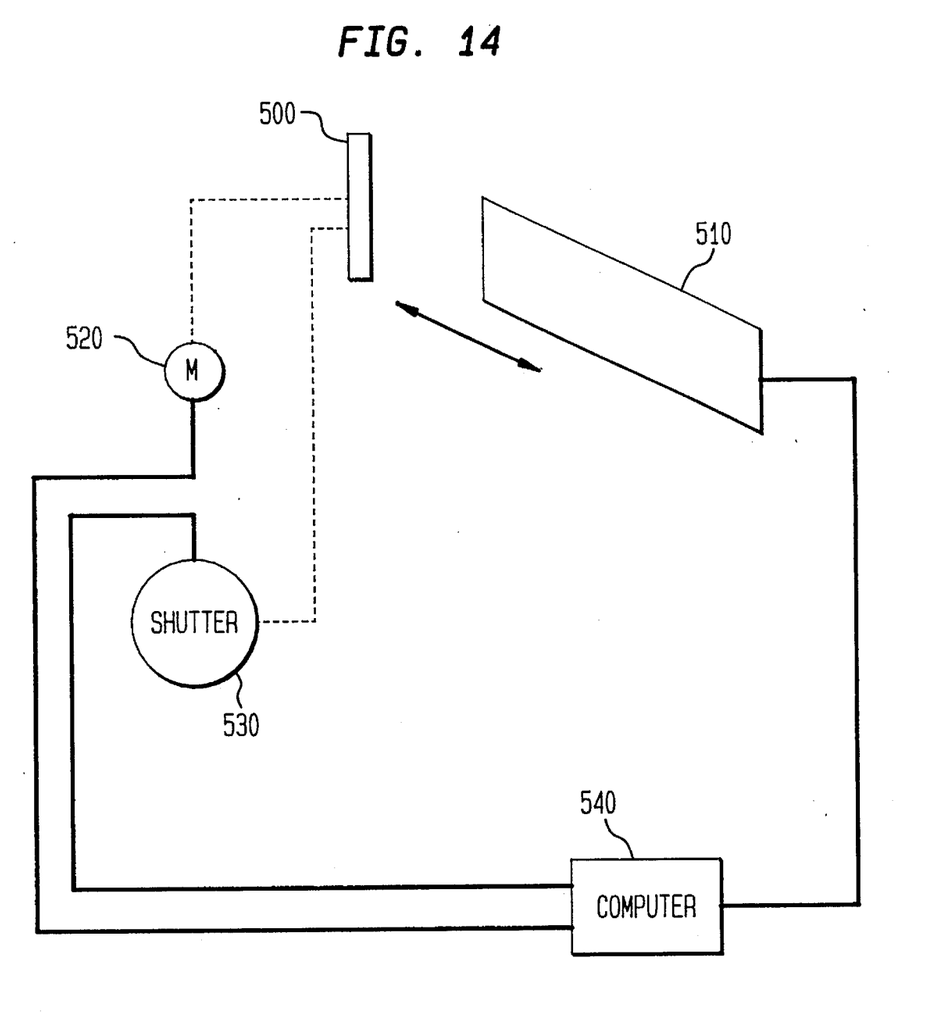
FIG. 14 is a block diagram of a scintillation camera system in accordance with the invention.

Apparatus in accordance with the preferred embodiment of the invention is illustrated in FIG. 14. As can be seen there, a scanning line source 500 is scanned across a detector 510 by operation of a motor 520. The shuttering of the line source 500 is controlled by a shutter mechanism 530. The detector 510, the motor 520 and the shutter mechanism 530 are all connected to a computer 540, which causes the motor 520 and the shutter mechanism 530 to be appropriately operated. During an initial step, the motor 520 is operated at high speed to scan across the detector 510 and the detector 510 feeds transmission CT data to the computer 540. The computer 540 processes the data to determine the count density registered at the detector 510 as a function of location. During a subsequent step, the computer 540 causes the motor 520 and the shutter mechanism 530 to be appropriately operated during a rescan of the detector 510 as described above.

Although a preferred embodiment has been described above, the scope of the invention is limited only by the following claims:

We claim:

1. A scintillation camera system that carries out attenuation correction, comprising:

means for supporting a patient;

at least one scintillation camera detector;

a gantry for rotating said at least one detector about an axis of rotation;

computer means, operatively connected at least to said gantry and said at least one detector, for collecting SPECT data and transmission CT data and reconstructing tomographic images from the SPECT data;

a line source, the line source being parallel to said axis of rotation; and means for scanning the line source in a plane while maintaining the line source parallel to said axis of rotation, said means being operatively connected to said computer means.

2. The system of claim 1, further comprising means for varying the radiation density of the line source.

3. The system of claim 2, wherein said varying means is operatively connected to said computer means.

4. A scintillation camera system that carries out attenuation correction, comprising:

means for supporting a patient;

at least one scintillation camera detector;

a gantry for rotating said at least one detector about an axis of rotation;

computer means, operatively connected at least to said gantry and said at least one detector, for collecting SPECT data and transmission CT data and reconstructing tomographic images from the SPECT data;

a line source, the line source being parallel to said axis of rotation; and means for scanning the line source in a plane while maintaining the line source parallel to said axis of rotation, said means being capable of moving the line source at at least one selected speed within a range of speeds and being operatively connected to said computer means.

5. The system of claim 4, further comprising means for varying the radiation density output by the line source.

6. A method of acquiring transmission CT data for carrying out attenuation correction on SPECT data, comprising the following steps:

placing a patient in such a position that the patient is interposed between a line source and a scintillation camera detector and the line source is parallel to the patient's body axis;

adjusting the line source to output radiation at a density that is less than maximum;

scanning the line source across the patient and thereby acquiring preliminary transmission CT data at the detector, said scanning being carried out at maximum speed in a plane that is parallel to the detector; and rescanning the line source across the patient and thereby acquiring additional transmission CT data at the detector, said rescanning being carried out at less than maximum speed in a plane that is parallel to the detector.

7. The method of claim 6, further comprising the step of varying radiation density from the source during said rescanning step.

8. The method of claim 7, further comprising the step of varying speed during said rescanning step.

9. The method of claim 6, further comprising the step of varying speed during said rescanning step.

* * * * *